(12) United States Patent
Murphy et al.

(10) Patent No.: US 7,238,365 B1
(45) Date of Patent: Jul. 3, 2007

(54) PESTICIDE FORMULATION

(75) Inventors: Dennis Lee Murphy, Flower Mound, TX (US); Jeanne Ann Witte, Carrollton, TX (US); Kim Wenn Yang, Dallas, TX (US); Joe Doyle McDaniel, Jr., Carrollton, TX (US)

(73) Assignee: Wellmark International, Schaumburg, IL (US)

( * ) Notice: Subject to any disclaimer, the term of this patent is extended or adjusted under 35 U.S.C. 154(b) by 0 days.

(21) Appl. No.: 11/054,134

(22) Filed: Feb. 8, 2005

(51) Int. Cl.
*A01N 37/06* (2006.01)

(52) U.S. Cl. .................. 424/438; 424/405; 424/406; 424/410; 424/442; 426/2; 514/549

(58) Field of Classification Search ............... 424/438, 424/442, 405, 406, 410; 514/549; 426/2
See application file for complete search history.

(56) References Cited

U.S. PATENT DOCUMENTS 5,439,924 A * 8/1995 Miller .................. 514/345
2004/0167034 A1 * 8/2004 Coote et al. .......... 504/358

* cited by examiner

*Primary Examiner*—Neil S. Levy
(74) *Attorney, Agent, or Firm*—Townsend and Townsend and Crew LLP (57) ABSTRACT

The present invention provides formulations which greatly improve the physical and chemical stability of pesticides such as insect growth regulators, in liquid feeds, and liquid feed supplements. The present invention prevents or reduces stratification in liquid feeds and liquid feed supplements.

17 Claims, 6 Drawing Sheets

PESTICIDE FORMULATION

BACKGROUND OF THE INVENTION

Liquid feeds and liquid feed supplements for economic and companion animals can be formulated to deliver a complete supplemental package for a full-range of diets. Such liquid feeds and liquid feed supplements can supply protein, mineral, additives and vitamin nutrition necessary to support desired performance levels. In general, these "liquid" products are suspensions of protein sources, and actually contain about 60–70% dry materials. However, no matter how well-balanced a diet, or how effective an additive, the feed offered must be eaten to be effective.

Ideally, a ration would reach every animal exactly as it was formulated, with each bite throughout the day representing the desired mix of ingredients and additives. In reality, feedstuffs can separate in the bunk, and animals may sort for preferred portions of the diet (i.e., grain), eating them first. If a pesticide were to be contained within the liquid feed, it would be important that it stay uniformly mixed throughout. Otherwise, undesired dosing could occur.

In view of the foregoing, there is a need in the art for economic and companion liquid feed and liquid feed supplement, which contains a pesticide, to remain uniformly mixed. A liquid feed which eliminates stratification in animal feed such as in a holding tank or a lick tank, is highly desirable. The present invention satisfies these and other needs.

SUMMARY OF THE INVENTION

The present invention provides a pesticidal formulation designed to be admixed with liquid feeds and liquid feed supplements. The pesticidal formulation (e.g., emulsion) of the present invention extends uniformity by reducing or eliminating stratification. That is, the pesticidal formulation (e.g., emulsion) is produced as a concentrate which, when admixed into a liquid feed or liquid feed supplement, has the surprising characteristic that it reduces or eliminates stratification of the active ingredient in the liquid feed or liquid feed supplement. As a result, the liquid feed or liquid feed supplement having the pesticide formulation admixed therein, is usable for a longer period of time in the field than pesticide products heretofore known. The pesticide formulation can take various forms, including, but not limited to, a wettable powder, an emulsion concentrate, a liquid concentrate, and a water soluble or dispersible granule or solid.

As such, in one embodiment, the present invention provides a pesticidal formulation, comprising:
 a) a pesticide; and
 b) a uniformity-extending agent, wherein the pesticidal formulation generates uniform dispersion in a liquid feed over an extended period of time.

In a preferred embodiment the present invention provides a stabilized pesticide emulsion, comprising:
 a) a pesticide optionally comprising a hydrophobic agent;
 b) a surfactant; and
 c) a uniformity-extending agent, wherein the stabilized pesticide emulsion is designed for liquid feed.

In another embodiment, the present invention provides a method for controlling an insect on livestock, comprising: administering a stabilized pesticide formulation (e.g., emulsion) as a feed-through product to livestock; and allowing the feed-through product to pass through the cattle into manure, wherein the pesticide is released into the manure thereby controlling the insect.

In yet another embodiment, the present invention provides a method for preparing a stabilized pesticide emulsion, the method comprising:
 admixing water and a uniformity-extending agent to form an aqueous premix;
 admixing a pesticide optionally comprising a hydrophobic agent with a surfactant to form an oil premix; and
 adding the oil premix to the aqueous premix to form the stabilized liquid pesticide emulsion.

Advantageously, the present invention greatly improves the uniformity of pesticides, such as insect growth regulators [IGR], in liquid feeds and liquid feed supplements for economic and companion animals. Prior to the advent of the present invention, stratification in the holding tank and lick tank occurred and insect growth regulators were not obtainable for the animal to properly self-dose by feeding. Dosing was erratic and without uniformity of the IGR, the product utility was brief. The present invention prevents or reduces liquid feed stratification of insect growth regulators in liquid feeds and liquid feed supplements. The present invention prolongs uniformity in the holding tank and lick tank many fold and prevents stratification. Surprisingly, this invention delivers to the feeding animal the correct IGR dosage to control certain insects in manure. These and other objects, embodiments and advantages will become more apparent when read with the drawings and detailed description which follow.

DETAILED DESCRIPTION OF THE INVENTION

I. General

The present invention provides pesticide formulations, methods of treating animals using pesticide formulations and methods of making pesticide formulations. In certain instances, the pesticide formulations can be added to liquid feeds and liquid feed supplements to reduce, and/or eliminate stratification in animal feed such as in a holding tank or lick tank. Advantageously, in certain aspects, the pesticidal formulation (e.g., emulsion) of the present invention can be used in feed-through products to treat and control insect infestation in livestock, for example, cattle. Various insects can be controlled and treated using the formulations and methods of the present invention. These include, but are not limited to, face flies, house flies, stable flies and horn flies. Horn flies are especially susceptible to the formulations and methods of the present invention.

In certain preferred aspects, the present invention provides a pesticidal formulation, which when added to liquid feed, stays uniformly mixed. In this manner, it is possible to deliver the correct dosage by for example, a feed product to ensure uniformity of dosing. The formulation has greatly reduced or eliminated settling, separation or stratification of the pesticide in the free flowing liquid feed. The pesticide formulation can take various forms, including, but not limited to, a wettable powder, an emulsion concentrate, molasses or water-based IGR liquid concentrate, and a water soluble granule.

II. Pesticides

Various pesticides for example, insecticides, can be used in the present invention. In a preferred aspect, an insecticide of the present invention is an insect growth regulator (IGR). Insect growth regulators (including juvenile hormones) are well known for their use and efficacy in controlling or eliminating insect infestation on humans, on animals, and in farm, ranch, residential and industrial environments. Many types of insects are controllable by insect growth regulators, including flies (e.g., face flies, house flies, stable flies and horn flies), fleas, mosquitoes, flour beetles, cigarette beetles, and cockroaches. The regulators vary widely in chemical composition, and two of the more prominent classes are 2,4-dienoic acids and phenoxyphenoxy compounds, particularly phenoxyphenoxyalkoxyheterocyclics, as well as benzoylureas and triazine derivatives. Examples of 2,4-dienoic acids and related compounds are methoprene, hydroprene, neotenin, and epiphenonane. As used herein, "methoprene" includes R-methoprene, S-methoprene and mixtures of R and S methoprene at all percentages of either isomer. S-methoprene is the preferred methoprene. Examples of phenoxyphenoxy compounds are fenoxycarb and pyriproxyfen. Examples of benzoylureas are lufenuron, diflubenzuron, terflubenzuron, triflumaron, hexaflumaron, and flucycloxuron. An example of a triazine derivative is 2-cyclopropylamino-4,6-bis(dimethylamino)-s-triazine.

The following IGR are suitable for the present invention. Chitin synthesis inhibitors are suitable such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron, and triflumuron. In addition, juvenile hormone mimics are suitable such as epofenonane, fenoxycarb, hydroprene, kinoprene, methoprene, pyriproxyfen, and triprene. Further, juvenile hormones are suitable such as juvenile hormone I, juvenile hormone II, and juvenile hormone III. Other suitable IGRs include, molting hormone agonists, chromafenozide, halofenozide, and methoxyfenozide tebufenozide. Moreover, molting hormones such as α-ecdysone, and ecdysterone are suitable. In addition, molting inhibitors such as diofenolan and other IGRs, which include precocenes, such as precocene I, precocene II, and precocene III are suitable. Finally, unclassified insect growth regulators are suitable such as dicyclanil. Preferred IGRs include methoprene, hydroprene, kinoprene, fenoxycarb, pyriproxyfen, and mixtures thereof. In the most preferred embodiment, methoprene is the IGR of choice.

In certain other aspects, the pesticide is an adulticide. Adulticides include organophosphates and neonicotinoids. In one aspect, the organophosphate insecticide is tetrachlorvinphos. In certain other aspects, the neonicotinoid insecticide is for example, imidacloprid, acetamiprid or thiomethoxam.

In certain aspects, the concentration of the pesticide in the formulation (e.g., emulsion) is about 0.000625% to about 50% w/w, preferably, 0.01% to about 10.5% w/w, and more preferably, 0.02% to about 2.0% w/w. In the most preferred embodiment, S-methoprene is the IGR of choice.

In certain embodiments, the pesticide can be formulated as a water dispersible granule or powder. The pesticidal formulations of the present invention can also comprise a wettable powder, spray, emulsion, colloid, aqueous or organic solution, dust, pellet, or colloidal concentrate. Dry forms of the pesticidal compositions may be formulated to dissolve immediately upon wetting, or alternatively, dissolve in a controlled-release, sustained-release, or other time-dependent manner.

A. Formulations

In certain embodiments, the present invention provides a pesticidal formulation, comprising: a) a pesticide; and b) a uniformity-extending agent, wherein the pesticidal formulation generates uniform dispersion in a liquid feed over an extended period of time. The pesticidal formulations can be manufactured into e.g., emulsion concentrates, solutions, oil in water emulsions, wettable powders, soluble powders, suspension concentrates, dusts, granules, water dispersible granules, tablets, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants.

The formulations of the invention can for example, be formulated as wettable powders, water dispersible granules, dusts, granules, solutions, emulsifiable concentrates, emulsions, suspension concentrates and aerosols. Wettable powders usually contain 1.0 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder, but without a dispersant, and may be diluted with a solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystallization or as antifreeze agents for water.

B. Hydrophobic Agent

Various hydrophobic agents are suitable for the present invention. In certain aspects, the hydrophobic solvent is a fat, vegetable oil, mineral oil or a combination thereof. The fat or vegetable oil can be for example, a mono-glyceride, a di-glyceride, a tri-glyceride or a mixture thereof. In certain aspects, the mineral oil is an aliphatic oil, a paraffinic oil, an isoparaffinic oil or a mixture thereof.

In certain aspects, the ratio of the hydrophobic agent to pesticide in the emulsion is about 0% to about 10% w/w, preferably 1% to about 6% w/w, and more preferably 2% to about 4% w/w.

C. Surfactant

Various surfactants are suitable for the present invention. These include, but are not limited to, a nonionic surfactant, an ionic surfactant or an amphoteric surfactant. The nonionic surfactant can be for example, polysorbate or polyethoxylated castor oil. In certain other aspects, the ionic surfactant is derived from a lecithin. In other embodiments, the surfactant is derived from a methyl glucoside coconut oil ester.

In certain aspects, the ratio of the surfactant to pesticide is about 1% w/w to about 20% w/w, preferably 2% w/w to about 15% w/w, and more preferably, 4% to about 10% w/w.

D. Uniformity-Extending Agent

In certain preferred aspects, the uniformity-extending agent is a carbohydrate (e.g. saccharide). Suitable carbohydrates include monosaccharides, oligosaccharides, polysaccharides and mixtures thereof. Suitable polysaccharides include, for example, a cyclodextrin, a starch, a carboxymethyl cellulose salt, an alginate, a methyl cellulose, an ethyl cellulose, a hydroxypropyl cellulose, sucrose, a starch glycolic acid salt, a molasses, lactose and dextrin. In certain aspects, the saccharide is a water soluble saccharide. In one preferred embodiment, the uniformity extending agent is molasses. Other suitable agents include, acacia, agar, guar, locust bean, tragacanth, xanthan, gums, or combinations thereof. In a preferred embodiment, the uniformity extending agent is molasses. Suitable types of molasses include, but are not limited to, beet sugar molasses, citrus molasses, hemicellulose extract, starch molasses, cane sugar molasses, and combinations thereof. Those of skill in the art will know of other types of molasses suitable for use in the present invention. Advantageously, the present of a uniformity extending agent affords protection against chemical oxidation and UV degradation.

In certain aspects, the ratio of the uniformity extending agent to pesticide is about 0.01% w/w to about 2% w/w, preferably about 0.05 to about 1.0% w/w, and more preferably, about 0.1% w/w to about 0.4% w/w.

In certain aspects, the formulations of the present invention further comprise an antioxidant. Suitable antioxidants include, but are not limited to, tocopherol, ascorbyl palmitate, propyl gallate, butylated hydroxyanisole (BHA), butylated hydroxytoluene (BHT), and combinations thereof.

In certain aspects, the ratio of the antioxidant to pesticide is about 0.001% w/w to about 2% w/w, preferably about 0.01% to about 1% w/w, and more preferably, about 0.1% to about 0.5% w/w.

E. Other agents

Various other agents are suitable for the present invention. These include, but are not limited to, a monohydric or a polyhydric alcohol. Suitable polyhydric alcohols are glycerol, 1,3-butylene glycol and propylene glycol. Suitable monohydric alcohols include pentanol, hexanol or mixtures thereof. All possible isomers such as normal or branched chain alcohols, are suitable for the present invention.

In certain aspects, the present formulations also contain other stability agents such as clays (e.g. kaolin), magnesium or aluminum silicates for extended physical stability of the feed product, as well as combinations of clays and gums.

III. Methods of Making

In another embodiment, the present invention provides a method for preparing a stabilized pesticide emulsion, comprising:

admixing water and a uniformity-extending agent to form an aqueous premix;

admixing a pesticide optionally comprising a hydrophobic agent with a surfactant to form an oil premix; and adding the oil premix to the aqueous premix to form the stabilized liquid pesticide emulsion.

Figure 1:
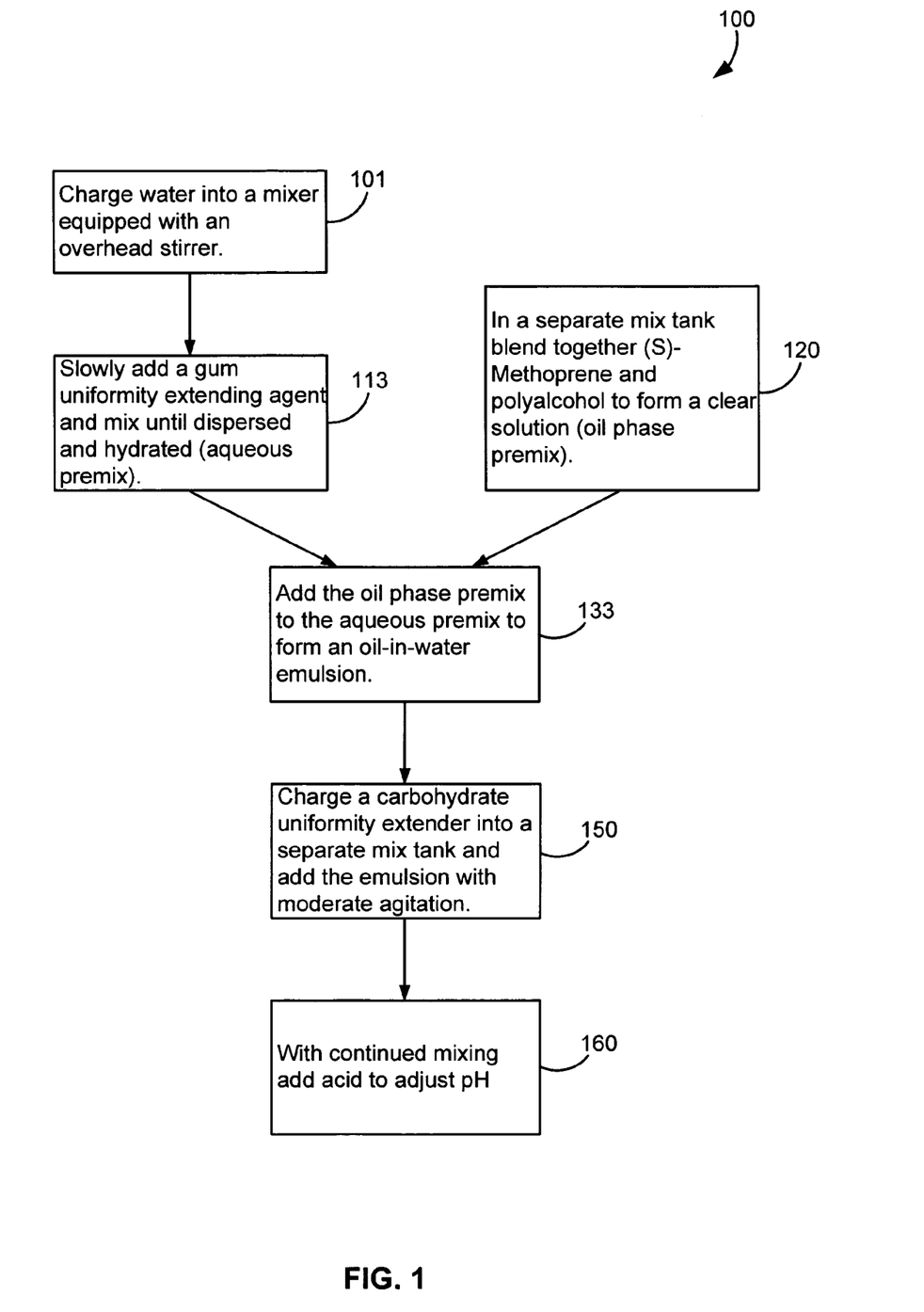
FIG. 1 shows a schematic of a process of the present invention.

FIG. 1 shows an exemplary process 100 for preparing the pesticide emulsion of the present invention. As shown therein, in certain aspects, water is charged into a mixer 101 equipped with for example, an overhead stirrer. Next, a gum uniformity-extending agent 113 is slowly added and mixed until the uniformity-extending agent is dispersed and hydrated to generate an aqueous premix. In a separate tank 120, a pesticide such as (S)-methoprene, and a poly alcohol are blended to form a clear solution to form an oil phase premix. The oil phase premix 133 is added to the aqueous premix to form an oil-in-water emulsion. A carbohydrate uniformity extending agent is charged 150 into a separate mix tank and added to the emulsion with moderate agitation. In certain aspects, an acid or base 160 is added to adjust pH. In certain preferred aspects, the pH of the emulsion is about 4.0 to 8.0, more preferably 5.0 to 7.0.

IV. Uses

Figure 2:
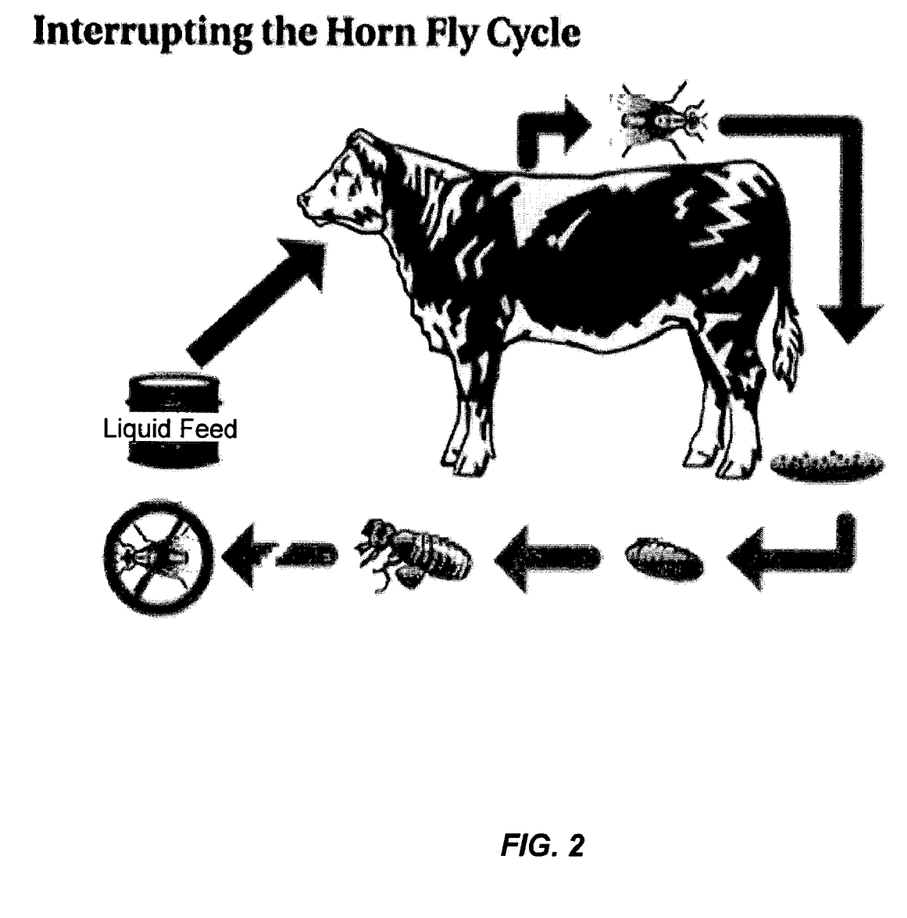
FIG. 2 shows a schematic of a use of the present invention.

In still other embodiments, the present invention provides a method for controlling or treating an insect on an animal such as cattle. As shown in FIG. 2, the method includes administering a pesticide formulation as a feed-through product to the animal, wherein the pesticide formulation is formulated into a final form such as a liquid feed ration. The feed-through product is allowed to pass through the animal into its manure. The pesticide is released in the manure, thereby controlling the insect.

In one example, cattle are unacceptably infested with horn flies. Adult horn flies live 2 to 4 weeks piercing the hide and sucking 20 to 30 blood meals a day from the cattle. The pesticide formulation of the present invention is ingested with the cattle's liquid feed. As they graze, cattle disperse the IGR via their manure. The present invention breaks the life cycle of the horn fly by, for example, preventing pupae from molting into adults. In 1 to 2 days, eggs laid in the IGR treated manure hatch into larvae. After 3 to 5 days, the larvae molt into pupae. Preferably, the present invention prevents adult emergence following pupal stage and the horn fly cycle has been broken.

In certain instances, the pesticide formulations can be added to liquid feed and liquid feed supplements to eliminate stratification in livestock feed such as in a holding tank. In certain aspects, the ratio of the pesticidal formulation (e.g., emulsion) to liquid feed is about 0.003% w/w to about 4% w/w, preferably, 0.0625% w/w to about 3% w/w and more preferably, 0.005% w/w to about 2% w/w. Surprisingly, when the pesticidal formulation (e.g., emulsion) is admixed into a liquid based livestock feed, the pesticidal formulation (e.g., emulsion) maintains physical stability and uniform dispersion over an extended period of time as well as maintaining chemical stability in the liquid feed.

In certain aspects, the pesticide formulation can be used in for example, liquid feed, used as a top dressing to cattle feed or used as a spray-on for livestock feed.

V. Stability

In certain aspects, the pesticide formulations (e.g., emulsion) of the present invention are physically stable. As used herein, the term "physically stable" means that stratification in liquid feed will not occur for at least 126 days. In certain aspects, the pesticide formulation (e.g., emulsion) is physically stable for a period of between about 30 days to about 150 days. In preferred aspects, the pesticide formulation (e.g., emulsion) is physically stable for a period of between about 90 days to 125 days. In other aspects, the pesticide formulations are physically stable for a period of between 50 days to 300 days, such as 100 days to 252 days. Moreover, in certain aspects, the pesticide formulation (e.g., emulsion) reduces and/or eliminates stratification in animal feed in a holding tank.

VI. Examples

These examples illustrate features of the inventive formulation.

Uniformity Test Method

This method is an assay to assess physical stability. The emulsified IGR liquid concentrate of the present invention is added to approx. 1,000 mls of liquid molasses. They are mixed together well and a duplicate sample is taken for an initial data point to assay for the active ingredient (S)-methoprene concentration value by an analytical method. Next, the molasses mixture is poured into a Pyrex clear glass 1,000 ml graduated cylinder. The top of the graduated cylinder is covered tightly with Parafilm M and then foil is placed over the top. This sample remains stored at room temperature.

For each data point, a Pyrex glass tube that is ½ inch diameter is used with a pipette bulb to slowly sample from the top, middle, or bottom of the graduated cylinder. After sampling from the desired layer the tube is slowly pulled out, and the outside of the tube is wiped clean before releasing the sample into a glass bottle. Each sample is prepared and analyzed separately for the active ingredient and to indicate if the emulsified (S)-methoprene IGR liquid concentrate is still suspended uniformly throughout the column for a period of time.

Example 1

This example shows a comparison of the inventive formulation versus a comparative formulation.

Figure 3A:
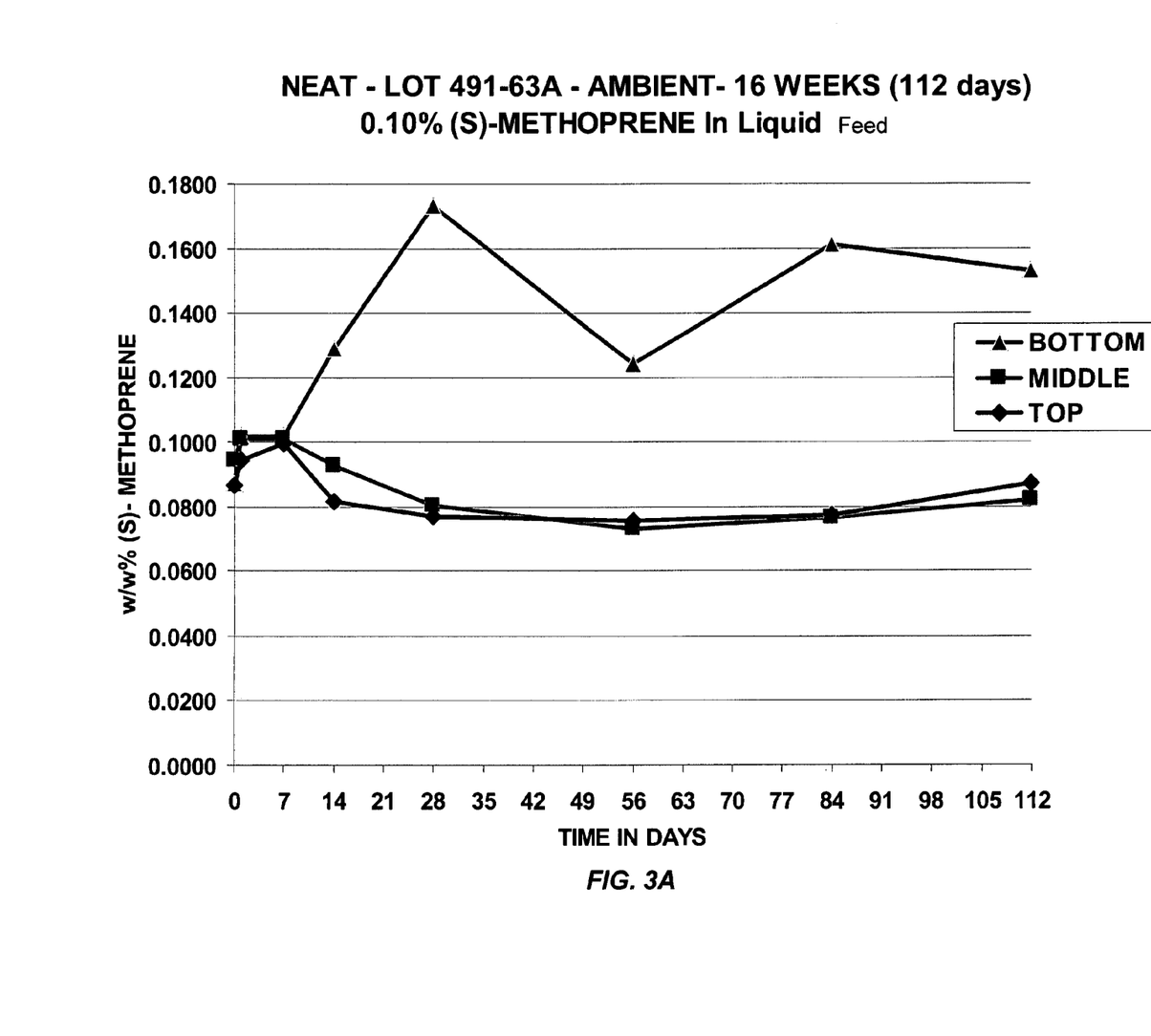
FIGS. 3A–C shows a comparison of an embodiment of a pesticide formulation of present invention versus other pesticide formations.
Figure 3B:
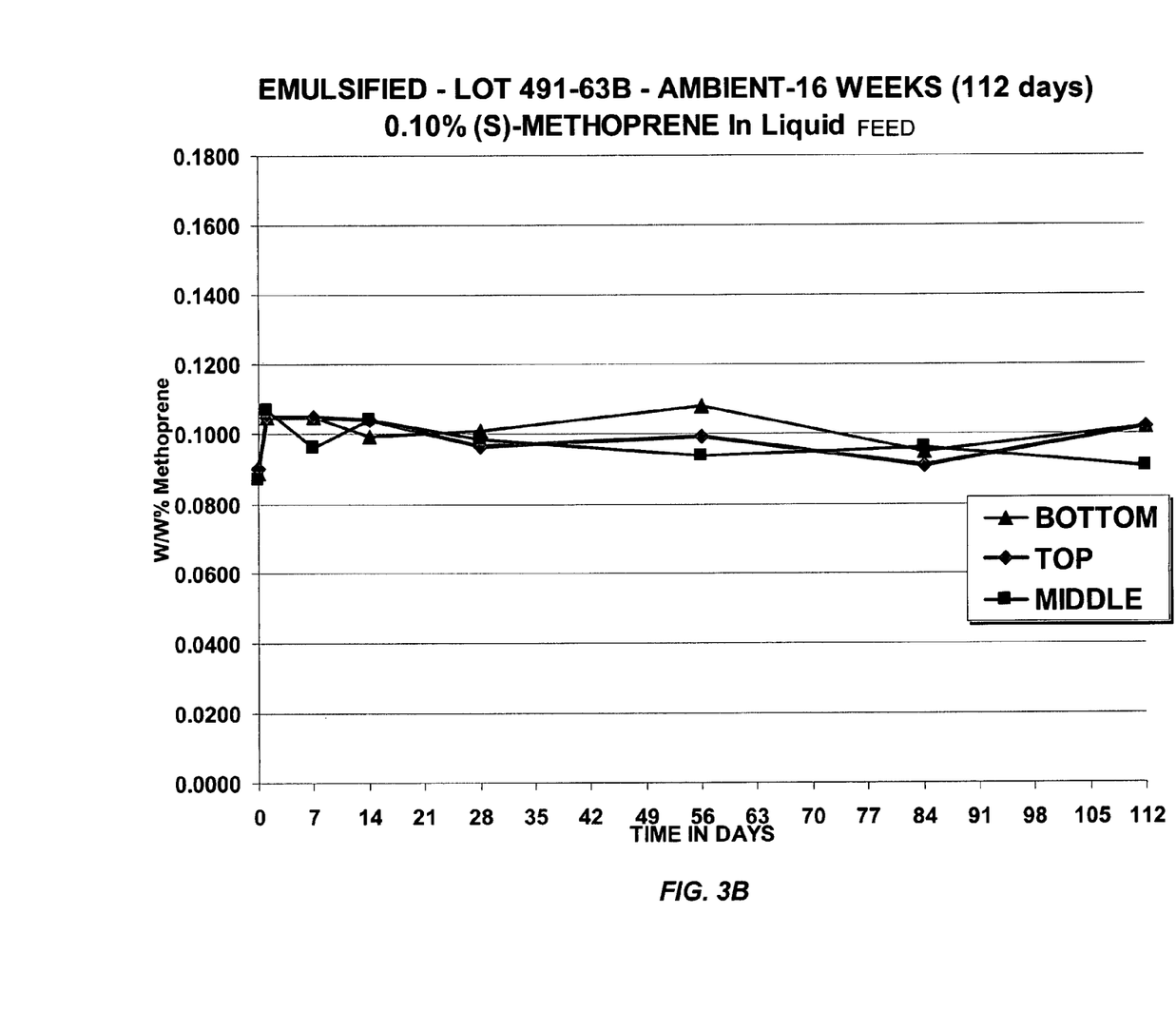
Figure 3C:
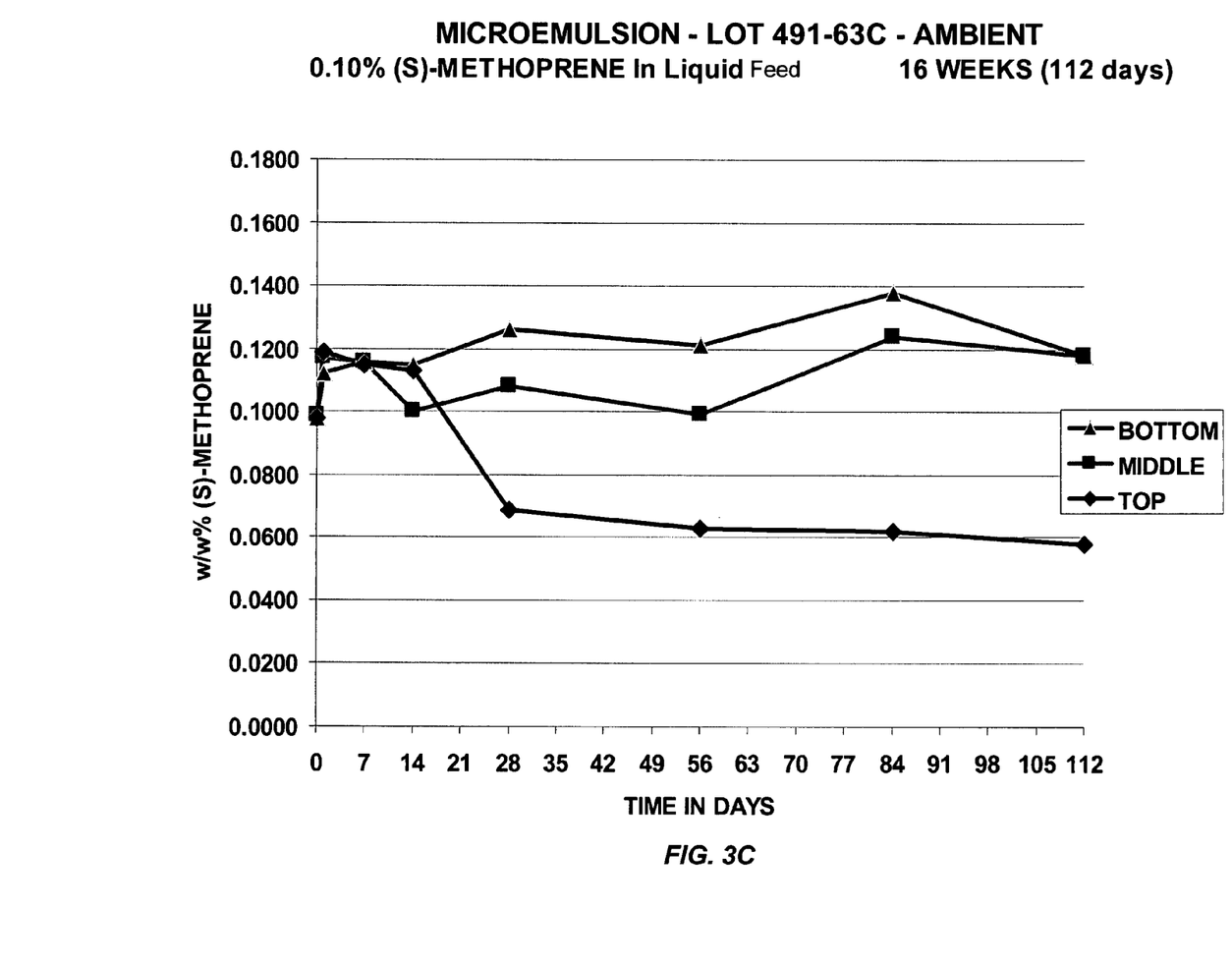

FIG. 3 A–C show the results as time (days) versus w/w % of the active ingredient (S)-methoprene. A straight line charted for top, middle, and bottom of (S)-methoprene values indicate uniformity.

As shown in FIG. 3A, the comparative neat solution of (S)-methoprene is non-uniform as the aliquots derived from the bottom show a higher proportion of pesticide. In addition, the top and middle layers decrease in pesticide concentration as a function of time, whereas the bottom layer tends up in concentration. This indicates that the solution is stratified.

As shown in FIG. 3B, the inventive emulsified solution of (S)-methoprene is uniform as the aliquots derived from the bottom, middle and top layers show uniform pesticide concentration. This indicates that the solution is homogeneous for extended periods of time. Advantageously, the emulsified solution will ensure uniform dosing of the pesticide.

As shown in FIG. 3C, the comparative microemulsified solution of (S)-methoprene is non-uniform as the aliquots derived from the bottom show a higher proportion of pesticide. The top and middle layers decrease in pesticide concentration. This indicates that the comparative solution is stratified.

Example 2

This example shows a water dispersible formulation of the present invention.

Water dispersible granules of the present invention were prepared having a size between 0.15 mm and 2.0 mm manufactured using the following procedure: (S)-methoprene with an antioxidant, a liquid emulsifying agent such as polysorbate (Tween or Span, or the like), are first mixed. It is then added to a mixture of dry powder/granule which consists of water soluble solid such as granule sugar(s), water soluble emulsifying agent such gums to make a granule product. Other adjuvant(s) such as binders, lubricants and the like can be added as needed depending on the granulating process used.

The granule when dissolved in water will result to an emulsion or micro-emulsion. It can also be added to a liquid feed directly without making an emulsion first.

Example Formula:

| Ingredients | % W/W |
|---|---|
| (S)-methoprene (94.0%) | 1.06 |
| Polysorbate | 0.50 |
| Tocopherol | 0.25 |
| Food Grade Sea Weed Gum | 0.50 |
| Sucrose, fine granule | 89.69 |
| Syrup (Binder) | 10.00 |
| Total Dry Solid % | 100.00 |

Manufacture Procedure:
1. Mix methoprene, polysorbate and tocopherol to a clear solution.
2. Mix gum and granulated sucrose together, making sure that the gum is finely divided and mixed with sucrose during the granulation process.
3. Pour or spray liquid premix in step 1 on powder premix of step 2 in a blender.
4. Push dough in step 3 through a granulator.
5. Dry the granule in step 4.
6. Using a granulator to grind the dry granule to desirable particle size.

Water Wettable Powder: methoprene with antioxidant, liquid emulsifying agents such as polysorbate (Tween or Span, etc), are mixed first. The liquid premix is then sprayed on a dry carrier.

Example Formula:

| Ingredients | % W/W |
|---|---|
| (S)-methoprene (94.0%) | 1.06 |
| Polysorbate | 0.50 |
| Tocopherol | 0.25 |
| Fine corn cob powder | 98.19 |
| Total % | 100.00 |

Manufacture Procedure:
1. Mix methoprene, polysorbate, tocopherol to a clear solution.
2. Spray on powder carrier.

S-methoprene with an antioxidant, liquid emulsifying agents such as polysorbate (Tween or Span, etc), and organic solvent if needed, are mixed to a uniform concentrated product. When this concentrated product is mixed with water, an emulsion or micro-emulsion will be obtained.

Example 3

This example shows a formulation of a 1% emulsion of the present invention.

Equipment Used: 3" Stainless propeller and a 3 liter stainless beaker.

Batch size: 8000 grams (Note 1)

Preparation of 1% emulsion:

2.98 grams of (S)-methoprene EC 33.6% mixed with 97.02 grams of D.I. water (2.98×33.6%)/100=1.0013%.

Mixing Procedure:
(1) 7920 grams of molasses is charged in the beaker fitted with the stirrer. Turn on the stirrer to the speed that a vortex is formed.
(2) Slowly add 80 grams of the 1% emulsion prepared above into the vortex.
(3) At the end of addition, move the beaker around to make sure that every part of the content is mixed. (Note 2)
(4) Total mixing time: 10 minutes.

Testing Procedure: Pour exactly 1 liter of the above product into a one liter cylinder after all the bubbles have escaped.

Sampling Procedure:
(1) Three ½ inch OD, 20" long Pyrex tubes were used.
(2) Sample from top, middle and bottom of the cylinder with top first and try not to stir up the content of the cylinder. A rubber pipet filler was used to suction the sample into the tube.
(3) For the top sample, the wiping of the tube is not necessary, for the middle and bottom sampling; the outside wall must be wiped clean with Kimwipes™ brand of lab tissue paper before inserting the tube into the sample jars. This is to prevent mixing up of Top, Middle, and Bottom samples.

Note 1. The rest of this batch was given to field development and they sent it outside for a cattle feeding test. In fact, this batch was prepared for biological evaluation and the biological results are very good.

Figure 4:
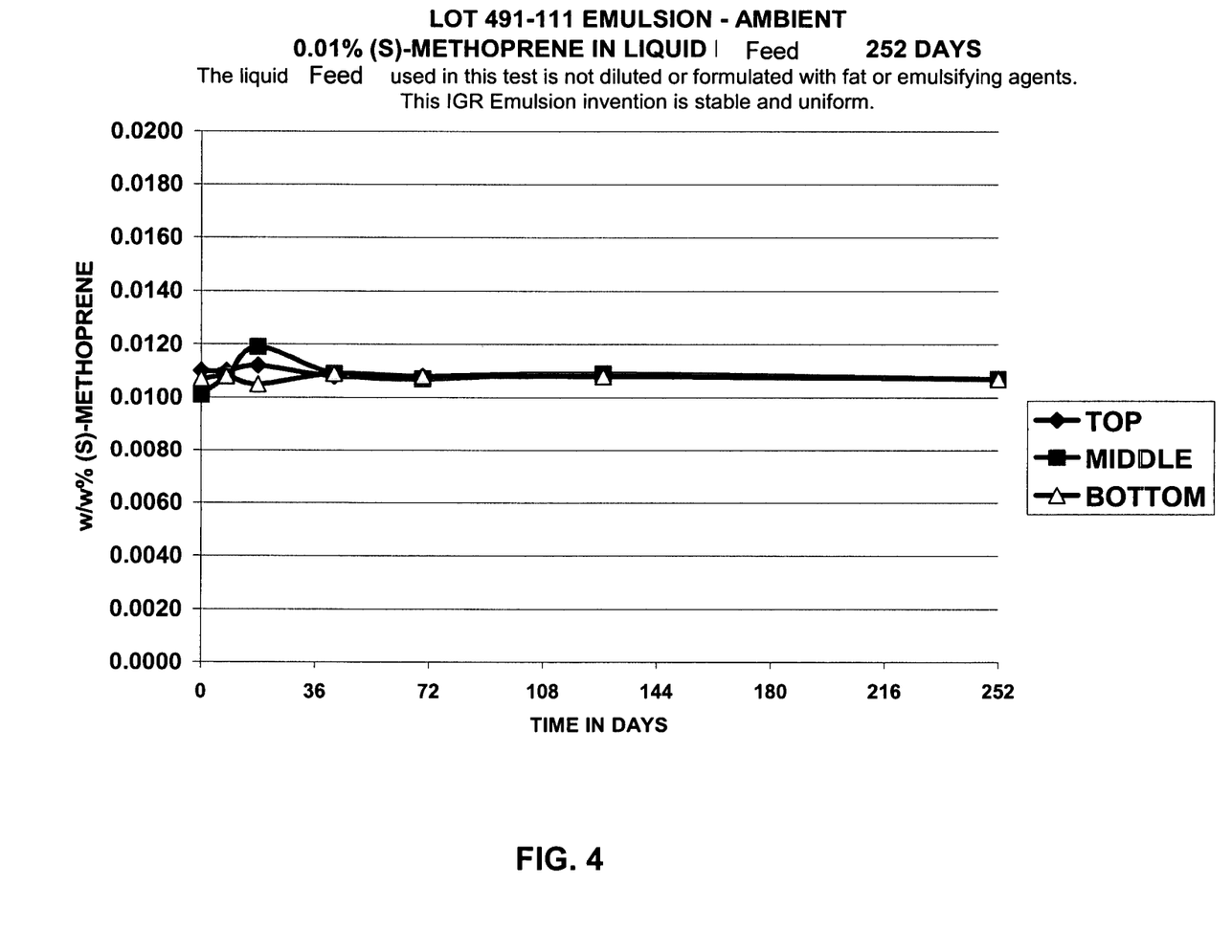
FIG. 4 shows the results of a physical and chemical stability test of an embodiment of the present invention.

Note 2. This 86 Brix Molasses is very viscous and special care is needed in the mixing. As shown in FIG. 4, the present invention has long stability and uniformity.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A stabilized pesticide formulation designed for liquid feed, wherein said formulation is a pesticide emulsion, said stabilized pesticide emulsion comprising:
    a) an insect growth regulator (IGR) pesticide comprising a hydrophobic agent, wherein said hydrophobic agent is a member selected from the group consisting a fat, vegetable oil, mineral oil and combinations thereof;
    b) a surfactant, wherein said surfactant is a member selected from the group consisting of a nonionic surfactant, an ionic surfactant and an amphoteric surfactant;
    c) a uniformity-extending agent, wherein said uniformity-extending agent is a carbohydrate; and
    d) a gum.

2. The emulsion of claim 1, wherein said IGR is a member selected from the group consisting of methoprene, hydroprene, kinoprene, fenoxycarb, pyriproxifen, cyromazine, dimilin, novaluron and mixtures thereof.

3. The emulsion of claim 2, wherein said insect growth regulator is methoprene.

4. The emulsion of claim 1, wherein said fat or vegetable oil is a member selected from the group consisting of a mono-glyceride, a di-glyceride, a tri-glyceride and mixtures thereof.

5. The emulsion of claim 1, wherein said mineral oil is a member selected from the group consisting of aliphatic oils, paraffinic oils, isoparaffinic oils and mixtures thereof.

6. The emulsion of claim 1, wherein said nonionic surfactant is a member selected from the group consisting of polysorbate and polyethoxylated castor oil.

7. The emulsion of claim 1, wherein when said emulsion is admixed into a liquid based animal feed, said emulsion maintains chemical stability in the liquid feed.

8. The emulsion of claim 1, wherein said emulsion is chemically stable.

9. The emulsion of claim 1, wherein said emulsion is physically stable.

10. The emulsion of claim 1, wherein said emulsion admixed into liquid feed eliminates stratification of the pesticide in liquid feed in a holding tank.

11. The emulsion of claim 1, wherein said gum is a member selected from the group consisting of acacia, agar, guar, locust bean, tragacanth, xanthan or combinations thereof.

12. The emulsion of claim 1, wherein when said emulsion is admixed into a liquid based animal feed, said emulsion maintains physical stability and uniform dispersion over an extended period of time.

13. The emulsion of claim 12, wherein said emulsion is physically stable for a period of between 50 days and 300 days.

14. The emulsion of claim 12, wherein said emulsion is physically stable for a period of between 100 days and 252 days.

15. The emulsion of claim 1, wherein said uniformity-extending agent is a carbohydrate selected from the group consisting of a monosaccharide, a polysaccharide, a cyclodextrin, a starch, a carboxymethyl cellulose salt, an alginate, a methyl cellulose, an ethyl cellulose, a hydroxypropyl cellulose, sucrose, a corn syrup, a starch glycolic acid salt, a molasses, lactose and dextrin.

16. The emulsion of claim 15, wherein said carbohydrate is a water soluble saccharide.

17. The emulsion of claim 15, wherein said uniformity extending agent is molasses.

* * * * *